United States Patent
Rothenwaender et al.

(10) Patent No.: US 8,936,104 B2
(45) Date of Patent: Jan. 20, 2015

(54) FLUID-DRIVEN MEDICAL OR DENTAL HANDLE

(75) Inventors: Michael Rothenwaender, Lamprechtshausen (AT); Karl Schmiedlechner, Ostermiething (AT); Norbert Schatz, Burmoos (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 719 days.

(21) Appl. No.: 13/283,480

(22) Filed: Oct. 27, 2011

(65) Prior Publication Data

US 2012/0111590 A1   May 10, 2012

(30) Foreign Application Priority Data

Nov. 5, 2010   (EP) .................................... 10190072

(51) Int. Cl.
*E21B 44/06* (2006.01)
*A61C 1/05* (2006.01)
*A61C 1/00* (2006.01)

(52) U.S. Cl.
CPC .. *A61C 1/05* (2013.01); *A61C 1/003* (2013.01)
USPC ............................................... 173/1; 173/169

(58) Field of Classification Search
USPC .................... 173/1, 12, 169; 433/32, 132, 99; 415/35, 904
See application file for complete search history.

(56) References Cited

U.S. PATENT DOCUMENTS

| | | | |
|---|---|---|---|
| 3,019,238 A * | 1/1962 | Schneider et al. ............ | 552/559 |
| 3,959,883 A * | 6/1976 | Walls et al. .................. | 433/98 |
| 4,276,024 A * | 6/1981 | Warrin ......................... | 433/99 |
| 4,744,752 A * | 5/1988 | Nakayama et al. ........... | 433/100 |
| 5,364,227 A * | 11/1994 | Franetzki et al. ............. | 415/35 |
| 5,507,642 A * | 4/1996 | Wohlgemuth ................ | 433/132 |
| 2008/0145817 A1 | 6/2008 | Brennan et al. | |
| 2008/0261172 A1* | 10/2008 | Rauchenzauner et al. .... | 433/132 |
| 2010/0055642 A1 | 3/2010 | Rothenwaender et al. | |

FOREIGN PATENT DOCUMENTS

| DE | 3246111 | 8/1983 |
|---|---|---|
| JP | 58-103448 | 6/1983 |

(Continued)

OTHER PUBLICATIONS

International Search Report for EP10190072 (mailed Aug. 17, 2011).

*Primary Examiner* — Andrew M Tecco
*Assistant Examiner* — Nathaniel Chukwurah
(74) *Attorney, Agent, or Firm* — Klarquist Sparkman, LLP

(57) ABSTRACT

A medical or dental, fluid-driven handle with a control or regulation circuit for the limiting, control or regulation to a maximum or predetermined rotational speed and a corresponding process are presented. The handle comprises a rotary part that can be set in rotary motion by a drive fluid, a fluid line carrying the drive fluid to or from the rotary part or a fluid branch line that is connected to a fluid line carrying drive fluid, and a control or regulation circuit designed to limit, control or regulate the rotational speed of the rotary part. An electrodynamic converter is driven by the rotary part for generating electrical energy and at least one actuator element is configured to act on the drive fluid. The actuator element is electrically connected to the electrodynamic converter such that it is supplied with electrical energy generated by the electrodynamic converter.

15 Claims, 6 Drawing Sheets

(56) References Cited

FOREIGN PATENT DOCUMENTS

| | | |
|---|---|---|
| JP | 05-212060 | 8/1993 |
| JP | 5-212060 | 8/1993 |
| JP | 05-245163 | 9/1993 |
| JP | 10-290810 | 11/1998 |
| JP | 11-033037 | 2/1999 |

* cited by examiner

FLUID-DRIVEN MEDICAL OR DENTAL HANDLE

CROSS REFERENCE TO RELATED APPLICATION

The present application claims priority from the pending European Patent Application No. 10190072.8, filed Nov. 5, 2010, which is incorporated herein by reference.

BACKGROUND

1. Field

This application relates to a fluid-driven medical or dental handle with a rotary part and a control or regulation circuit for the limiting, control or regulation of the rotational speed of the rotating part, and a process for the limiting, control or regulation of the rotational speed of the rotary part.

2. Description of Prior Art

The patent application US 2010/055642 A1, which is commonly owned, discloses a fluid-driven handle with a control or regulation circuit for rotary speed limiting. The handle comprises a rotary part that can be set in rotary motion by a drive fluid to drive a tool that can be connected to the rotary part, an electrodynamic converter driven by the rotary part for the induction of electric voltage and at least one switching element for the selectable opening and closing of an electric circuit between the two ends of a coil of the electrodynamic converter, so that with the electric circuit closed an electric current and an induction magnetic field braking the rotary speed of the rotary part and the tool that can be connected to it can be induced.

It would be advantageous to create a fluid-driven medical or dental handle with an alternative device for the limiting, controlling or regulation of the rotary speed.

SUMMARY

According to one embodiment, this is achieved by a medical or dental, fluid-driven handle comprising: a rotary part that can be set in rotary motion by a drive fluid to drive a tool that can be connected to the rotary part, a fluid line carrying the drive fluid to or from the rotary part or a fluid branch line that is connected to a fluid line carrying the drive fluid to or from the rotary part, and a control or regulation circuit that is designed to limit, control or regulate the rotational speed of the rotary part, wherein the control or regulation circuit has an electrodynamic converter for the generation of electric energy driven by the rotary part and at least one actuator element that is configured to act on the drive fluid flowing in the fluid line or the fluid branch line, wherein the at least one actuator element is electrically connected to the electrodynamic converter in such a way that the at least one actuator element can be supplied with the electric energy generated by the electrodynamic converter to carry out the actuation process.

The control or regulation circuit is thus designed as a control or regulation circuit acting on the drive fluid of the rotary part or as a pneumatic control or regulation circuit. The control or regulation circuit directly changes via the actuator element a parameter of the drive fluid, for example the fluid pressure or the volume flow, so that the rotational speed of the rotary part is limited, controlled, regulated or changed. The electrodynamic converter is thus designed as an energy source for the actuator element or for the actuation of the actuator element. At least a part of the electrical energy generated by the electrodynamic converter is thus provided or used for the actuation of the actuator element, for example to move a mobile component of the actuator element.

Preferably the at least one actuator element is also electrically connected to the electrodynamic converter in such a way that the effect of the actuator element on the drive fluid takes place depending on the rotational speed of the rotary part. The electrical energy generated by the electrodynamic converter is thus used for two purposes: first, it serves to cause the actuator element to act on the drive fluid or to carry out an actuation process acting on the drive fluid on the part of the actuator element, thus it is required by the actuator element for that element to carry out an actuation movement; and second, due to the particularly positive correlation between the electrical energy generated by the electrodynamic converter and the rotational speed of the rotary part (as the rotational speed increases the electrical energy generated increases and/or as the rotational speed decreases the electrical energy generated decreases), the rotational speed of the rotary part is determinable, preferably by a switching and/or control device. Thus, in accordance with a particularly preferred embodiment, it is possible to effect the action of the actuator element on the drive fluid only upon reaching or exceeding a predetermined rotational speed value or a predetermined value of the electrical energy generated by the electrodynamic converter (which is then at least partly used as a switching and/or control signal).

The electrodynamic converter, in the following also called the generator, preferably has a stator and a rotor, wherein the rotor is connected to the rotary part or is implemented as a part of the rotary part. The rotary part, for example, comprises the rotor of the handle acted upon by the drive fluid, a shaft rotationally mounted in the handle, for example a hollow shaft for the releasable support of the treatment tool, or the shaft of a tool that can be held in the handle. The rotor preferably comprises a magnetic element and the stator at least a coil, but of course the reverse arrangement is also possible. The magnetic element is preferably provided on the rotary part, so that the magnetic element can be set into motion by the rotary part. Preferably, the magnetic element is designed as a permanent magnet, particularly as a disc magnet, that is fastened to the rotary part. Alternatively, the rotary part can itself be magnetic, for example due to being manufactured of a magnetic material or by being magnetised.

The control or regulation circuit limits, controls or regulates the rotational speed of the rotary part and the tool that can be connected to it to a maximum or set value, in particular under low load or idling of the handle, in order to reduce the noise emission of the handle and to reduce the mechanical stress on the ball bearings located in the handle that support the rotary part. Rotational speed limiting also permits gentler application of the tool to the point of treatment. In accordance with one embodiment, the control or regulation circuit is designed to limit the rotational speed of the rotary part and of the tool to a value in a range from about 300,000-150,000 rpm, preferably to a value in the range from about 275,000-200,000 rpm, and particularly preferably to about 250,000 rpm.

In accordance with one embodiment, the at least one coil is wound around a soft magnetic coil core that concentrates the magnetic flux of the magnetic element of the generator and guides it to the coil. In particular, the soft magnetic coil core that comprises one or more layers, preferably electrically isolated from one another, is ring-shaped and surrounds the outer circumference of the magnetic element. This simplifies their installation in the handle, particularly when the electrodynamic converter comprises multiple coils.

In accordance with another embodiment, the at least one actuator element is implemented as an actuator element, particularly a mechanical one that can be driven by electrical energy, for example a valve, particularly a control valve or a proportional valve, particularly preferably as a solenoid valve or a throttle. The valve or the throttle are preferably located directly on or in the line for the drive fluid to or from the rotary part or directly on or in the fluid branch line.

According to another embodiment, the fluid branch line connects the fluid line carrying the drive fluid to the rotary part and the fluid line carrying the drive fluid from the rotary part. Alternatively, the fluid branch line can diverge from the fluid line carrying the drive fluid to the rotary part and open into a hollow chamber of a hollow outer shell of the handle. Both alternatives thus have the advantage that they permit a portion of the drive fluid unnecessary for driving the rotary part to be drained through the fluid branch line.

To achieve even operation of the rotary part, according to one embodiment the fluid line carrying the drive fluid to or from the rotary part has an auxiliary line that bypasses the actuator element, so that at least a part of the drive fluid can bypass the actuator element. The supply of the rotary part with drive fluid is thus composed of a continuously flowing or constant drive fluid stream and a variable drive fluid stream that can be changed by the action of the actuator element.

According to one embodiment, the control or regulation circuit has a switching and/or control device designed for the selective supply of the at least one actuator element with electric energy generated by the electrodynamic converter, depending on the rotational speed of the rotary part. As already explained earlier, this makes it possible to make the action of the actuator element on the drive fluid depend on the rotational speed of the rotary part, or to control the action of the actuator element on the drive fluid depending on the rotational speed of the rotary part. The electrical energy generated by the electrodynamic converter (due to the direct relationship between the rotational speed of the rotary part and the electrical energy generated) is preferably at least partly also used as a switching and/or control signal. The switching and/or control device preferably permits the supply of the actuator element with electrical energy generated by the electrodynamic converter or action of the actuator element on the drive fluid only if the rotational speed of the rotary part has achieved or exceeded a predetermined value, for example about 200,000 rpm or about 250,000 rpm or about 275,000 rpm.

According to a preferred embodiment, the switching and/or control device has a device for determining the rotational speed of the rotary part. The device for determining the rotational speed of the rotary part can be implemented by components that, for example, use directly or indirectly the electrical energy generated by the electrodynamic converter or a value of the electrical energy generated by the electrodynamic converter for the determination of the rotational speed of the rotary part. Such components can particularly be implemented using a microcontroller or by a radiation source and a semiconductor element receiving a radiation, as will be explained in more detail below.

Alternatively, the device for determining the rotational speed of the rotary part can have components that do not derive the rotational speed of the rotary part from the electrical energy generated by the electrodynamic converter. Such components can for example be implemented by a sensor for the detection of pressure variations in the drive fluid, in particular by a microphone that detects the sound that is emitted by the rotary part and that changes depending on the rotational speed or changes in the rate of flow velocity of the drive fluid, or by an optical detection device, which for example detects radiation emitted or reflected by the rotary part or conducted by or through the rotary part.

According to a particularly preferred embodiment, the switching and/or control device comprises a microcontroller that is electrically connected to the electrodynamic converter and that is designed to compare a value of the electrical energy generated by the electrodynamic converter, particularly the voltage, with a predetermined limit value and to permit the supply of the actuator element with the electrical energy generated by the electrodynamic converter, if the value of the electrical energy generated by the electrodynamic converter reaches or exceeds the predetermined value.

According to an alternative embodiment, the switching and/or control device comprises a radiation source and a radiation receiving sensor, particularly a semiconductor element, for example a photodiode, wherein the radiation source can be supplied with electrical energy from the electrodynamic converter and the radiation receiving sensor is located in such a way that it receives radiation emitted from the radiation source, so that an electric circuit can be closed between the electrodynamic converter and the actuator element and the actuator element can be supplied with electrical energy generated by the electrodynamic converter when the sensor detects that the radiation source is emitting radiation or emitting radiation that exceeds a predetermined limit value. The radiation source is particularly designed in such a way that it only emits radiation when the electrical energy generated by the generator that is directed at the radiation source exceeds a threshold value. The radiation source is for example designed as a light-emitting diode.

According to a preferred embodiment, the electrodynamic converter is comprised of multiple coils, wherein at least a first coil is exclusively provided for the supply of the actuator element with electrical energy, particularly for carrying out the actuation process, and wherein at least a second coil is exclusively provided for the supply of the switching and/or control device with electrical energy, particularly for the generation of a switching and/or control signal for the actuator element. In this manner, in particular when multiple first coils are exclusively provided for the supply of the actuator element with electrical energy, a reliable and sufficient energy supply to the actuator element is ensured.

In order to achieve reliable function of the actuator element and preferably also of the switching and/or control device, according to one embodiment the control or regulation circuit has a device for the rectification of the electrical energy generated by the electrodynamic converter, so that the actuator element and preferably also the switching and/or control device can be supplied with direct current.

According to a preferred embodiment, the entire control or regulation circuit is housed in the handle and/or in a connecting part that can be connected to the handle, in particular in an adapter or in a coupling element. At least the actuator element, and preferably also the switching and/or control device, is independent of an electrical energy source located outside the handle and/or the connecting part. Thus, in an advantageous manner, the control or regulation circuit is fully functional when the handle is connected to a purely pneumatic supply unit.

A method for limiting, controlling or regulating the rotational speed of a medical or dental, fluid-driven handle having a rotary part that can be set in rotary motion by a drive fluid to drive a tool connected to the rotary part, the fluid line carrying the drive fluid to or from the rotary part or in a fluid branch line that is connected to the fluid line and a control or regulation circuit that is designed to limit, to control or to regulate the rotational speed of the rotary part, wherein the control or regulation circuit comprises an electrodynamic converter driven by the rotary part and at least one actuator element that is configured to act on the drive fluid flowing in the fluid line or the fluid branch line, wherein the at least one actuator element is electrically connected to the electrodynamic converter, wherein the method comprises driving the rotary part with the drive fluid, generating electrical energy with electrodynamic converter, supplying electrical energy from the electrodynamic converter to the at least one actuator element, and acting on the drive fluid flowing in the fluid line or the fluid branch line in an actuation process with the actuator element to the limit, control or regulate the rotational speed.

These and other embodiments will be described below with reference to the following drawings.

DETAILED DESCRIPTION

Figure 1:
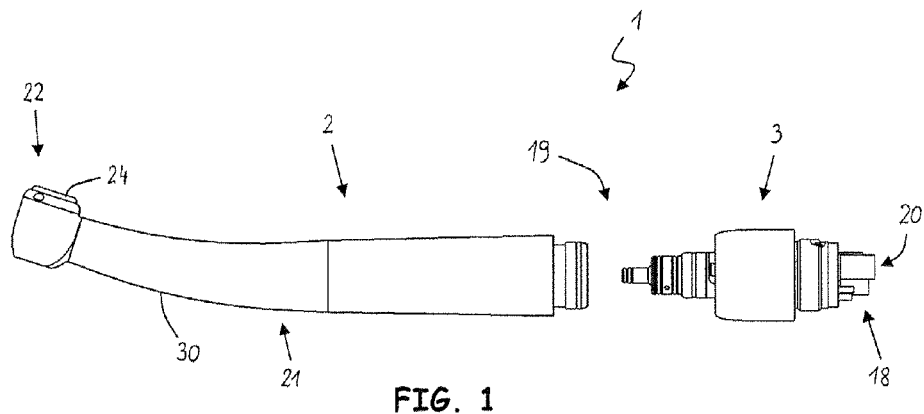
FIG. 1 shows an external view of a medical or dental, fluid-driven handle with a control or regulation circuit for the limiting, control or regulation of the rotational speed to a maximum or predetermined rotational speed value.

The medical or dental, fluid-driven handle 1 shown in FIG. 1 is designed as an elongated, pipe-shaped instrument that on one end has a connection 18 to one or more media sources, for example to a fluid source, particularly to a compressed air source. The handle 1 as shown in FIG. 1 comprises two parts, namely a handpiece 2 and a connecting part 3 that can connect to the handpiece 2 and that is designed for example as a coupling or adapter. The connecting part 3 and the handpiece 2 can be releasably connected together using a coupling device 19. The connection 18 provided on the supply end of the connecting part 3, as shown in FIG. 1, comprises multiple connection pieces 20, which connect lines or channels provided in the connecting part 3 with one or more media sources, particularly with a compressed air source, preferably also with a source for liquids. The lines or channels extend through the connecting part 3 and, preferably through the coupling device 19, carry the medium or media to the handpiece 2. Alternatively it is of course also possible that the handle 1 only comprises the handpiece 2 and that on the supply end of the handpiece 2 a connection similar or identical to connection 18 to one or more media sources is provided.

A control or regulation circuit 8 that is described below in more detail for the limiting, control or regulation of the rotational speed of a rotary part 4 to a rotational speed value is housed, preferably completely, in handle 1. According to different embodiments, the control or regulation circuit 8 is either completely housed in handpiece 2 or at least parts of the control or regulation circuit 8, particularly an actuator element 10, preferably a valve 10A, are located in the connecting part 3.

The handpiece 2 comprises a handle part 21 that is curved or has two segments arranged at an angle to one another, and an adjacent head part 2. On head part 22 there is provided a tool opening 23 (see FIG. 2) through which a tool can be releasably inserted into the head part 22. The tool opening 23 is arranged laterally on the head part 22, so that the tool projects out of the head part 22 at an angle to the handle part 21 or its longitudinal axis. On the end of the head part 22 opposite the tool opening 23 there is a push-button 24 provided that is operatively connected to a tool release device located in the head part 22 in order to release the tool from the head part 22. Of course, the handle 1 or the handpiece 2 can also have other known forms, for example a pistol shape or a straight-shaped implementation.

Figure 2:
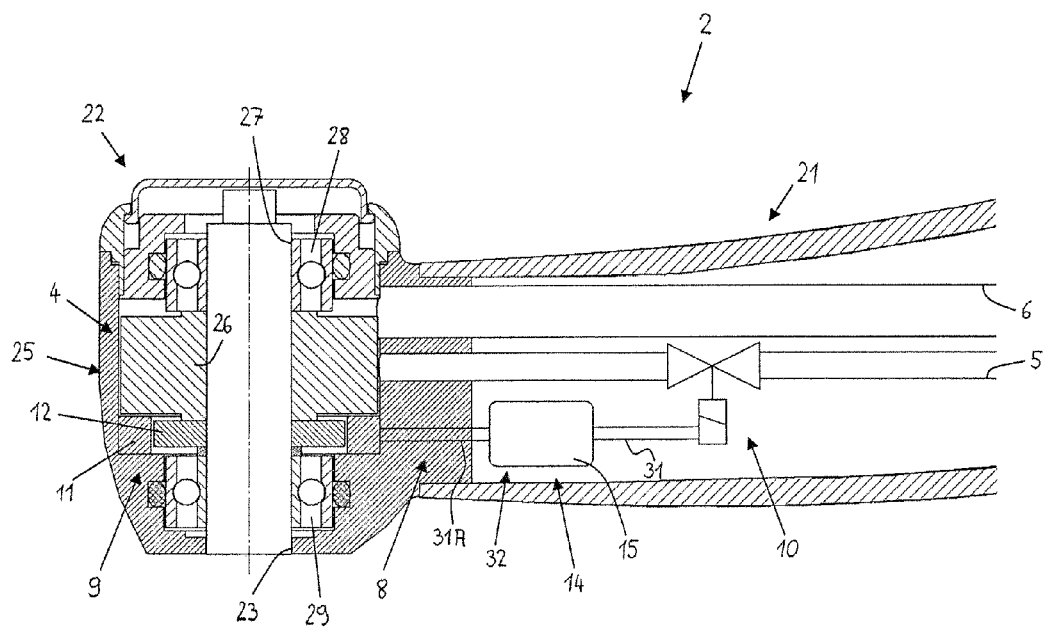
FIGS. 2 through 8 show cross sectional views of different embodiments of medical or dental, fluid-driven handpieces, with a control or regulation circuit for the limiting, control or regulation of the rotational speed to a maximum or predetermined rotational speed value, that have an actuator element that is supplied with electrical energy from an electrodynamic converter.

As can be seen in FIG. 2, a fluid line 5 carrying the drive fluid towards the head part 22 or to a rotary part 4 located in head part 22 and a fluid line 6 carrying the drive fluid away from the head part 22 or from the rotary part 4 located in the head part 22 extend through the handpiece 2, particularly through the handle part 21. Other media lines, for example one or more media lines for cooling media, optical light guides or electrical lines, may also extend through the handpiece 2. The fluid line 5 carries the drive fluid, for example compressed air or water, to a drive unit 25 that comprises at least a rotary part 4 that can be set in rotary motion, for example an impeller, a rotor of an air or turbine motor, a shaft, a chucking device for the tool, etc.

According to the embodiment of the handpiece 2 shown in FIG. 2, the rotary part 4 comprises a rotor 26 and a hollow shaft 27 to which the rotor 26 is fastened and in which is located a chucking device for the tool or which is part of the chucking device. The rotary part 4 and the tool that can be connected to it are supported by two roller bearings 28, 29 in a rotary fashion in the handpiece 2. The roller bearings 28, 29 are supported on rotationally fixed components of the handpiece 2, for example the outer shell 30 (see FIG. 1).

In the head part 22 of the handpiece 2 there is provided an electrodynamic converter or generator 9 comprising a rotor and a stator. The stator is formed of at least one, preferably multiple, coils 11 and preferably of a soft magnetic coil core around which the coils 11 are wound. The coils 11 and the coil core surround the rotor which has a magnetic element 12, or are located near the rotor. As shown in FIG. 2, the rotor comprises a magnetic element 12 connected to the rotary part 4 which can be set into rotational motion with the rotary part 4, in particular a disc-shaped magnetic element with a hole through which the hollow shaft 27 extends. Instead of a separate magnetic element it is also possible to implement the rotary part 4 or a part thereof magnetically, for example by magnetising it. Preferably the rotor 26 is at least partly magnetic, in particular the blades of the rotor 26 are magnetic.

The fluid line 5 ends near the rotary part 4 or the rotor 26, and introduces the drive fluid to rotary part 4, particularly the rotor 26, or into a hollow chamber in the head part 22 in which the rotary part 4 or the rotor 26 are supported. By subjecting the rotor 26 to the drive fluid from the fluid line 5, the rotor 26 is set in rotary motion and thus the electrodynamic converter 9 is also activated and a voltage is induced in the coils 11. The magnitude of the voltage induced in the coils 11 thereby correlates with the rotational speed of the rotor, the rotary part 4 and the tool.

The generator 9 is a part of the control or regulation circuit 8 for the limiting, control or regulation of the rotational speed of the rotary part 4 and/or of a tool connected to the rotary part 4. According to the embodiment shown in FIG. 2, the control or regulation circuit 8 comprises not only the generator 9 but also an actuator element 10 that can be driven by electrical energy, a switching and/or control device 14 and electric lines 31, 31A that connect the generator 9 to the switching and/or control device 14 and the actuator element 10. The actuator element 10, implemented as a valve, particularly as a control valve or a proportional valve, acts on the drive fluid flowing in the fluid line 5 by means of an actuation process. For example, the actuator element 10 changes the fluid pressure or the volume flow of the drive fluid, particularly by changing the inner diameter of the fluid line 5 that the drive fluid can flow through, so that the rotational speed of the rotary part 4 can be changed.

The actuator element 10 receives electrical energy generated by generator 9 through the electric lines 31, 31A to carry out the actuation process. A part of the energy imparted to the rotary part 4 by the drive fluid is thus used for operation of the actuator element 10. If the rotational speed of the rotary part 4 is too high, then the actuator element 10 reduces the energy introduced to the rotary part 4, for example by reducing the fluid pressure or the volume flow of the drive fluid, whereby the rotational speed of the rotary part 4 falls. If the rotational speed of the rotary part 4 is too low, then the actuator element 10 increases the energy introduced to the rotary part 4, for example by increasing the fluid pressure or the volume flow of the drive fluid, so that the rotational speed of the rotary part 4 rises.

According to a simple embodiment not shown, the control or regulation circuit 8 comprises the generator 9 that can be driven by the rotary part 4, the actuator element 10, the electric lines 31, 31A to connect the generator 9 to the actuator element 10, and a part of the fluid line 5. Preferably, however, the control or regulation circuit 8 additionally contains a switching and/or control device 14 which supplies the actuator element 10 selectively with electrical energy generated by the generator 9, in particular depending on the rotational speed of the rotary part 4, and which particularly has a device 32 for determination of the rotational speed of the rotary part 4, as shown in FIG. 2. The switching and/or control device 14 shown in FIG. 2 is implemented as a microcomputer or a microcontroller 15 and connected electrically between the generator 9 and the actuator element 10.

The microcontroller 15 receives electrical energy generated by the generator 9 through the lines 31A and measures or determines a current parameter or value of the electrical energy, which correlates with the rotational speed of the rotary part 4, for example the voltage or the current. The microcontroller 15 or at least parts of the microcontroller 15 thus determine the rotational speed of the rotary part 4 and form the device 32 for determining the rotational speed of the rotary part 4. In microcontroller 15, furthermore, there is at least one limit value stored for the current parameter of the electrical energy, so that the microcontroller 15 can compare the current parameter with the limit value and selectively supply the actuator element 10 with electrical energy generated by the generator 9 depending on the relationship of the current parameter with the limit value. For example, the switching and/or control device 14 supplies the actuator element 10 with electrical energy or closes the circuit between the generator 9 and the actuator element 10 when the rotational speed of the rotary part 4 and thus the current parameter of the electrical energy generated by the generator 9 reaches or exceeds the limit value. Alternatively, the switching and/or control device 14 interrupts the supply of the actuator element 10 with electrical energy or opens the circuit between the generator 9 and the actuator element 10 when the rotational speed of the rotary part 4 and thus the current parameter of the electrical energy generated by the generator 9 reaches or falls below the limit value. Particularly preferably, the actuator element 10 that can be driven by electrical energy is implemented as a proportional valve, whereby the switching and/or control device 14 supplies the proportional valve with electrical energy in such a way that it carries out a continual actuation process depending on the rotational speed of the rotary part 4.

The other embodiments shown in FIGS. 3-8 of handpieces with a control or regulation circuit 8 for limiting, control or regulation of the rotational speed of the rotary part are similar in many regards to the structure and function of the handpiece 2 in FIG. 2. For this reason, particularly those features will be described below that differentiate the handpieces of FIGS. 3-8 from the handpiece 2 of FIG. 2.

Figure 3:
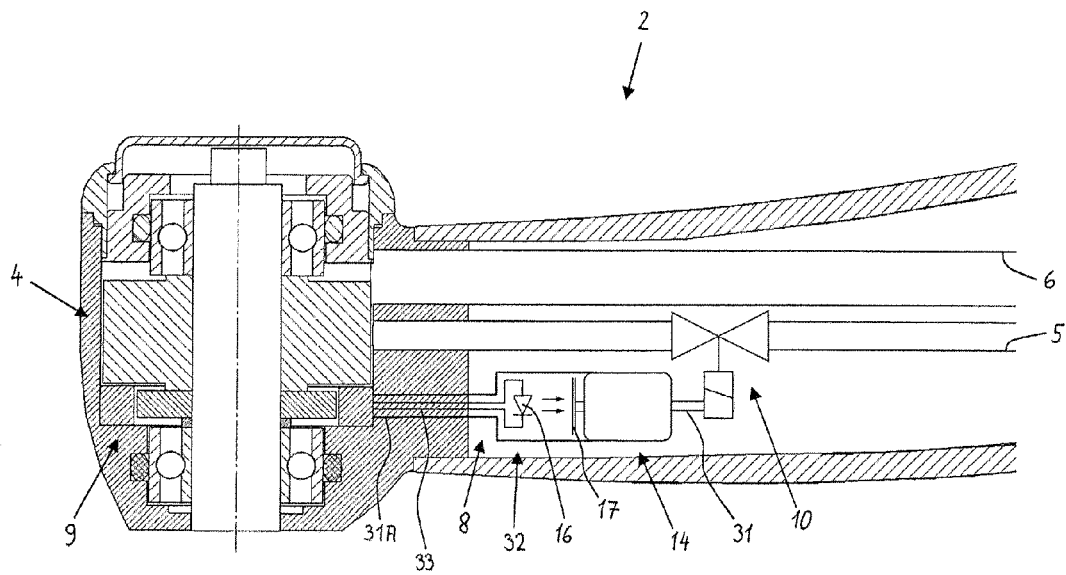

The control or regulation circuit 8 of handpiece 2 in FIG. 3 differs by an alternative design of the switching and/or control device 14 and/or by an alternative design of the device 32 for determining the rotational speed of the rotary part 4: Device 32 comprises a radiation source 16, for example one or more light-emitting diodes, and a radiation receiving sensor 17, for example a photodiode. The radiation source 16 can be supplied with electrical energy by the electrodynamic converter 9 through the electric lines 33. If the electrical energy generated by the generator 9 reaches or exceeds a predetermined value, for example the switching voltage or passing voltage of the light-emitting diode, then radiation source 16 emits electromagnetic radiation. The radiation-receiving sensor 17 is located and designed in such a way that it receives this radiation emitted by the radiation source 16. If the sensor 17 detects that the radiation source 16 emits radiation or emits radiation that exceeds a predetermined limit value, then the radiation-receiving sensor 17 and/or the switching and/or control device 14 close the circuit between the generator 9 and the actuator element 10, so that the actuator element 10 can be supplied with the electrical energy generated by the generator 9. If the radiation source 16 does not emit radiation or if the radiation source 16 emits radiation that falls below a predetermined limit value, the radiation-receiving semiconductor element 17 and/or the switching and/or control device 14 open the circuit between the generator 9 and the actuator element 10, so that the actuator element 10 is no longer supplied with the electrical energy generated by the generator 9. The switching and/or control device 14 preferably also has a microcontroller 15 that processes the signals from the sensor 17 and carries out the closing of the circuit. The actuator element 10, the sensor 17 and/or the switching and/or control device 14 are supplied with the electrical energy generated by the generator 9 via the electric lines 31A.

Figure 8:
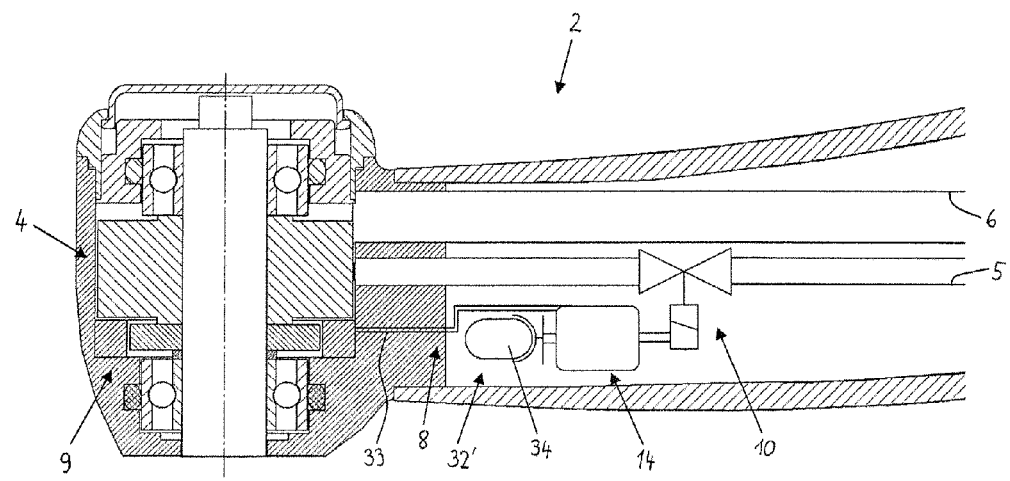

The devices 32 in FIGS. 2 and 3 each thus use (directly or indirectly) the electrical energy generated by the generator 9 or a value thereof for determining the rotational speed. Alternatively, FIG. 8 shows a device 32' for determining the rotational speed of the rotary part 4 which does not derive the rotational speed of the rotary part 4 from the electrical energy generated by the electrodynamic converter 9. The device 32' comprises a sensor for the detection of pressure variations in the drive fluid, for example a microphone 34, which detects the sound emitted by the rotary part 4 that changes depending on the rotational speed, or changes of the flow velocity of the drive fluid in the fluid lines 5 or 6. The switching and/or control device 14, which preferably also has a microcontroller 15, processes the signals from the device 32', i.e. from the microphone 34, and closes or opens or causes the closure or opening of the circuit between the generator 9 and the actuator element 10 depending on the rotational speed of the rotary part 4/the signals from the device 32'. The electrical energy generated by the generator 9, according to this embodiment, thus serves as the electrical supply for the actuator element 10, the switching and/or control device 14, and the device 32' (via the electric lines 33), but not for determining the rotational speed of the rotary part 4.

The device 32' for determining the rotational speed of the rotary part 4, which does not derive the rotational speed of the rotary part 4 from the electrical energy generated by the electrodynamic converter 9, can alternatively also be implemented with other components, for example by an optical detection device that detects radiation emitted or reflected by the rotary part 4 or conducted by or through the rotary part 4.

Figure 4:
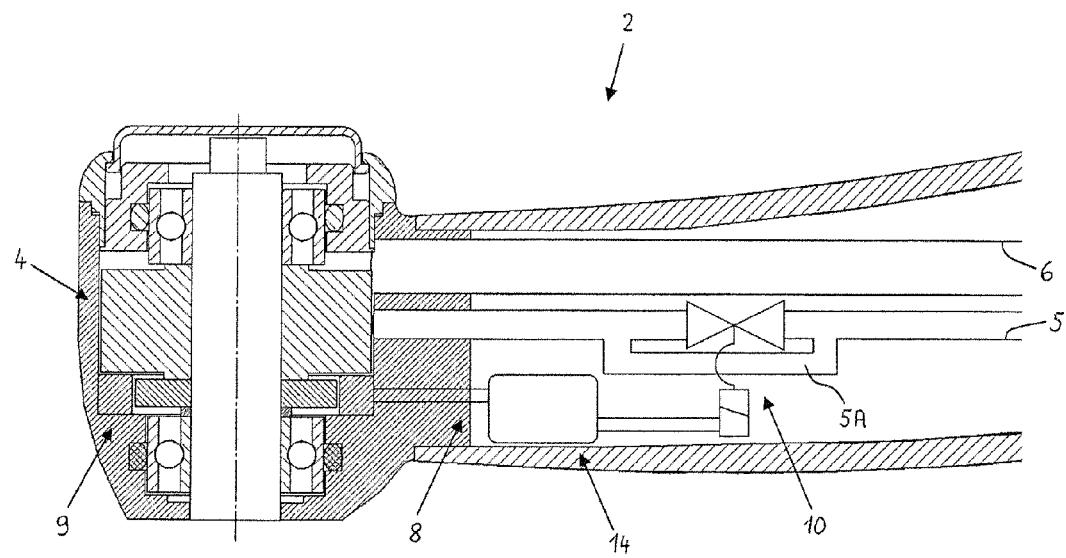

The handpiece 2 shown in FIG. 4 comprises a fluid line 5 for carrying the drive fluid to the rotary part 4 and an auxiliary line 5A of the fluid line 5 which bypasses the actuator element 10 provided in the fluid line 5. The auxiliary line 5A originates from the fluid line 5 before the actuator element 10 relative to the direction of flow of the drive fluid, and opens back into the fluid line 5 after the actuator element 10. Alternatively, it is also possible that auxiliary line 5A remains separate from the fluid line 5 up to the rotary part 4. At least a part of the drive fluid can thus be routed around the actuator element 10, permitting a calmer, more even drive of the rotary part 4. Of course, it is also possible to place the actuator element 10 in the auxiliary line 5A.

Figure 5:
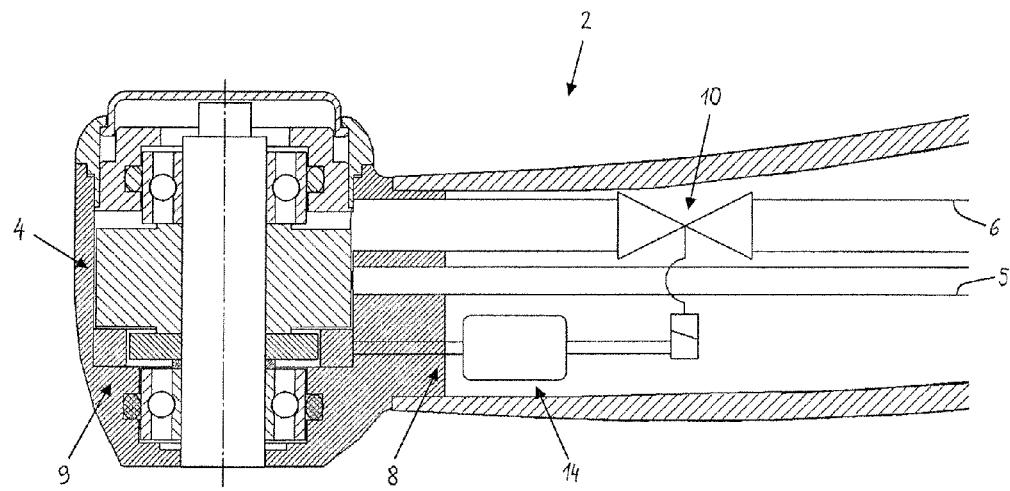

In the embodiment of the handpiece 2 shown in FIG. 5, the actuator element 10, which is again preferably implemented as a valve, is located in the fluid line 6 for carrying the drive fluid away from the rotary part 4 or head part 22.

Figure 6:
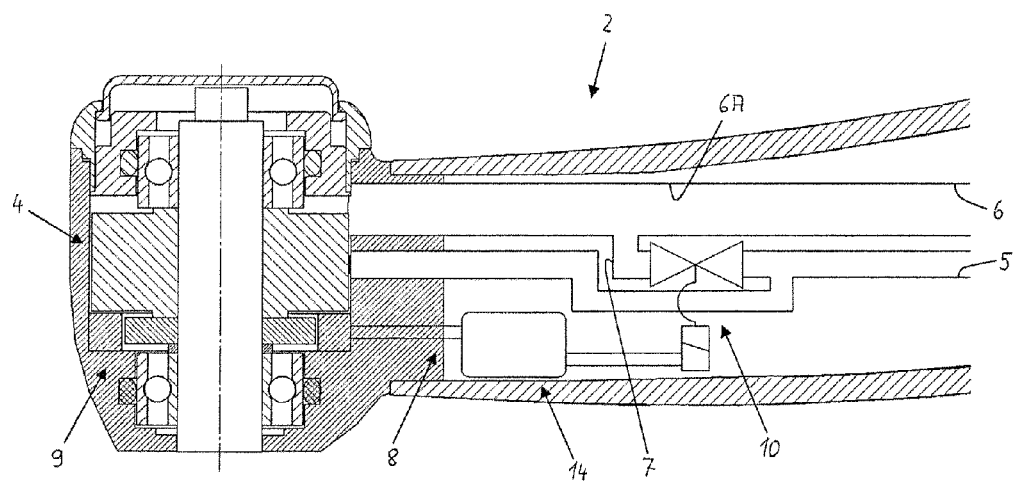
Figure 7:
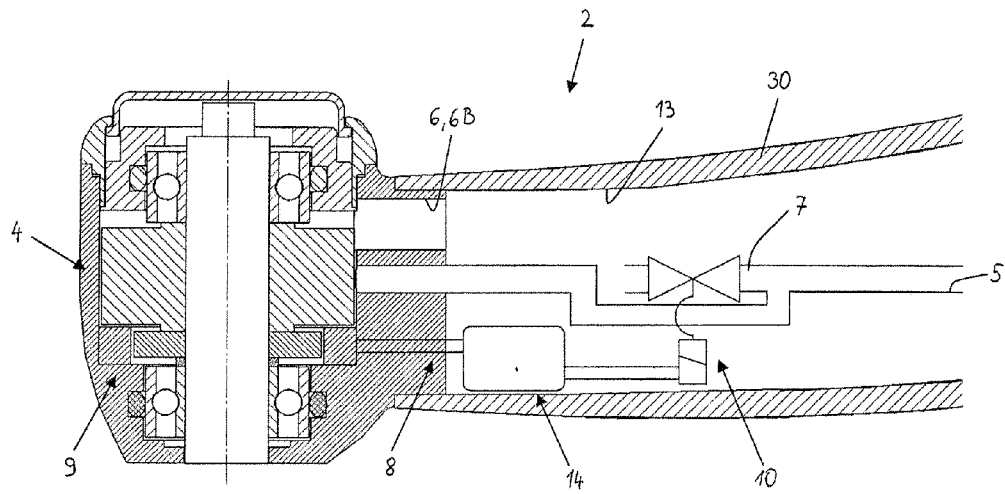

The handpieces 2 shown in FIGS. 6 and 7 each have a fluid branch line 7 that connects or short circuits the fluid line 5 carrying the drive fluid to the rotary part 4 and the fluid line 6 carrying the drive fluid from the rotary part 4. The actuator element 10, which is preferably implemented as a valve, is located in or on the fluid branch line 7. If the actuator element 10 is not completely closed, a part of the drive fluid flows directly from the fluid line 5 into fluid line 6. In the handpiece 2 shown in FIG. 6, the fluid branch line 7 opens into a segment 6A of fluid line 6 implemented as a pipe, or it is connected to the same.

In the handpiece 2 in FIG. 7, the fluid line 6 carrying the drive fluid from the rotary part 4 comprises only a short pipe-like segment 6B and is subsequently implemented by the outer shell 30 of the handpiece 2. The used drive fluid or the drive fluid flowing away from rotary part 4 thus flows through the hollow chamber 13 into the outer shell 30. The fluid branch line 7 in this embodiment also opens into the hollow chamber 13.

In the embodiments shown in FIGS. 2-8 the electrodynamic converter 9 supplies all components of the control or regulation circuit 8 with electrical energy, in particular the actuator element 10, the switching and/or control device 14 and the device 32 for determining the rotational speed of the rotary part 4. The control or regulation circuit 8 or the handle 1 thus require no electrical contact or lines connecting handle 1 with an external energy source, that is, one located outside handle 1.

Figure 9:
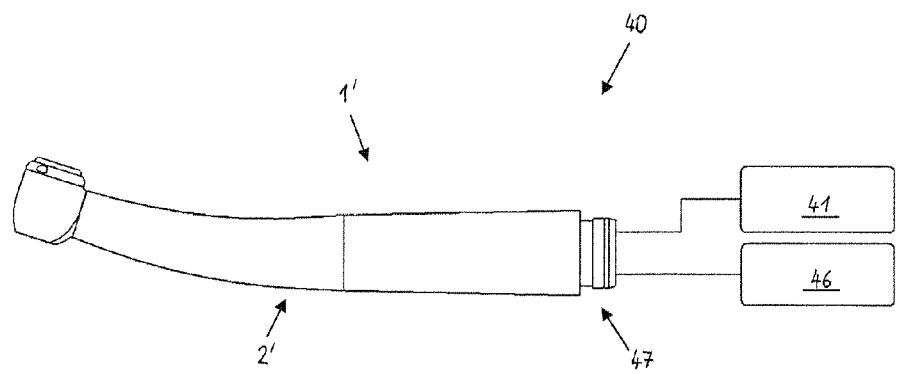
FIG. 9 shows a medical or dental treatment device with a control and/or regulation device for the control and/or regulation of the rotational speed of the rotary part.
Figure 10:
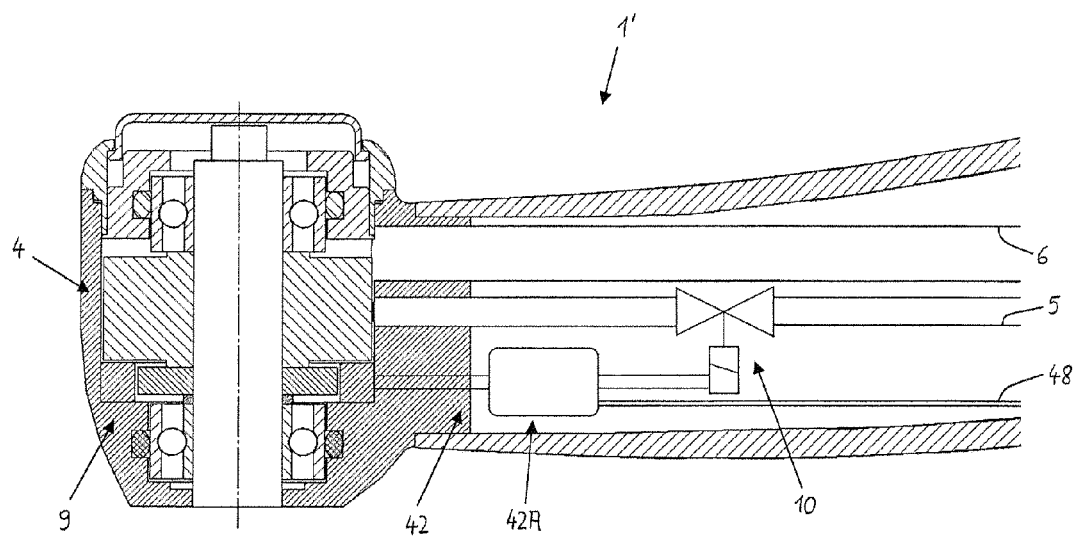
FIGS. 10 and 11 show cross sectional views through medical or dental, fluid-driven handpieces for use with a medical or dental treatment device in FIG. 9.
Figure 11:
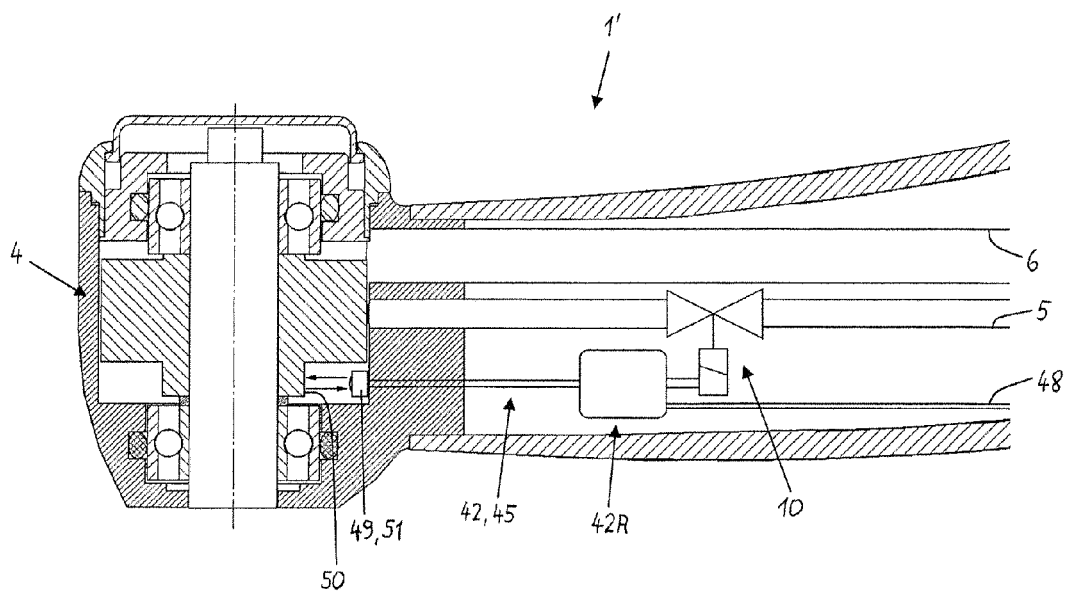

In contrast, the treatment device 40 and handles 1' shown in FIGS. 9-11 are designed in such a way that at least according to certain embodiments their control or regulation circuit can be at least partly operated by electrical energy which does not originate from the electrical energy source represented by the generator 9, in particular from an electrical energy source outside the handle 1'. The treatment device 40 and handles 1' in FIGS. 9-11 thus also have their own inventive aspect independent of the handles described above.

The medical or dental treatment device 40 comprises a handle 1', a rotary part 4 provided in the handle 1' that can be set into rotary motion by a drive fluid, for the driving of a tool that can be connected to the rotary part 4, a device 42, 42A for determining the rotational speed of the rotary part 4 and a control and/or regulation device 41 for the control and/or regulation of the rotational speed of the rotary part 4 that is designed to compare the rotational speed of the rotary part 4 determined by the device 42 for determining the rotational speed of the rotary part 4 with a set value and in the case of deviation of the detected rotational speed from the set value to operate an actuator element 10 that acts upon the drive fluid in order to limit the rotational speed of the rotary part 4 to the set value or to cause it to approach the set value, wherein the actuator element 10 is implemented as an actuator element 10 that is driven by electrical energy and that is located in the handle 1'.

The great advantage of the location of the actuator element 10 in the handle 1' is due to the fact that the distance between the actuator element 10 and the rotary part 4 is very small, so that the dead time, that is, the period of time between a change in the rotational speed and the reaction of the actuator element is also very small. Thus a stable operation of the treatment device 40 is obtained in an advantageous manner, in particularly without the risk of oscillation in the control or regulation circuit. Preferably the entire control or regulation circuit, which particularly comprises the device 42, 42A for determining the rotational speed of the rotary part 4, the control and/or regulation device 41 and the actuator element 10 can be driven with electrical energy and electrical signals, so that the operation of the control or regulation circuit is accelerated even further or the dead time reduced even further.

According to one embodiment, the actuator element 10 is implemented as a valve, particularly as a control valve, solenoid valve or proportional valve, or as a throttle.

The medical or dental treatment device 40 shown in FIG. 9 comprises a handle 1' that is designed substantially identically to the handle 1 shown in FIG. 1. The handle 1' comprises either only a handpiece 2' that is releasably connected via a coupling device 47 at least to a fluid source 46 and possibly also at least to parts of the control and/or regulation device 41, as shown in FIG. 9, or alternatively a handpiece 2' and a releasable connecting part 3, as can be seen in FIG. 1.

According to one embodiment, the medical or dental treatment device 40 furthermore comprises an energy source that provides electrical energy for the operation of the actuator element 10, wherein the energy source is located either in the handle 1' or outside the handle 1'. If the energy source is located in the handle 1', then it comprises for example a battery or a rechargeable battery or an electrodynamic converter 9 that can be driven by the drive fluid. The electrodynamic converter 9 or generator can preferably be directly or indirectly driven by the rotary part 4, as shown in FIG. 10.

The generator 9 of the handle 1' in FIG. 10, however, does not serve only or primarily to provide the energy supply of the actuator element 10, but is especially (due to the correlation described above between the rotational speed of the rotary part 4 and the electrical energy generated by the generator 9) a part of the device 42 for determining the rotational speed of the rotary part 4. The electrical energy generated by the electrodynamic converter 9 preferably serves exclusively to determine the rotational speed of the rotary part 4. In other words, the device 42 for determining the rotational speed of the rotary part 4 thus has an electrodynamic converter 9 that can be driven by the rotary part 4, so that the rotational speed of the rotary part 4 can be derived from the electrical energy generated by the electrodynamic converter 9. The device 42 is connected by electric lines 48 with the control and/or regulation device 41 and sends either the electrical energy generated by the generator 9 directly to the control and/or regulation device 41, or modifies the electrical energy generated by the generator 9 by means of a component 42A. The component 42A is for example implemented as an amplifier, rectifier, filter, analogue/digital converter or microcontroller. The electrical energy modified by component 42A is subsequently, particularly in the form of an electric rotational speed signal, directed through the electric lines 48 to the control and/or regulation device 41.

The control and/or regulation device 41 compares the electrical energy received from the device 42 or the rotational speed signal with a rotational speed set value that is fixed or can be changed by the user, and in case of deviation of the determined rotational speed from the set value operates the actuator element 10 by an electrical, control or regulation signal in such a way that it acts on the drive fluid so that the rotational speed of the rotary part 4 approaches the rotational speed set value or is limited to it, as already described above.

If the electrical energy generated by the electrodynamic converter 9 serves exclusively for the determination of the rotational speed of the rotary part 4, then the treatment device 40 comprises a separate energy source that supplies the actuator element 10 (by means of electric lines not shown) and possibly also the device 42 for determining the rotational speed of the rotary part 4, particularly component 42A, with electrical energy. This electrical energy source is preferably located outside the handle 1', in particular it is implemented as a part of the control and/or regulation device 41, wherein if necessary the electric lines 48 can also be used for the transmission of electrical energy. A releasable electrical connection between the actuator element 10 and the electrical energy source is particularly preferably provided, particularly as a part of the coupling device 47, for example sliding electrical contacts or electrical plug contacts.

Alternatively, it is also possible that the control and/or regulation device 41 for the control and/or regulation of the rotational speed of the rotary part 4 is completely located in the handle 1', for example in the component 42A or as a part of the component 42A. The generator 9 or the electrical energy generated by the generator 9 preferably also exclusively serves to determine the rotational speed of the rotary part 4, so that in this case the electric lines 48 are particularly used for the supply of the control and/or regulation device 41, of the device 42 for determining the rotational speed of the rotary part 4 and the actuator element 10 with electrical energy. Particularly preferably, the electrical energy is provided by an energy source outside the handle 1'.

According to an alternative embodiment, the device 42 for determining the rotational speed of the rotary part 4 has a sensor to detect pressure variations in the drive fluid, in particular a microphone 34 that detects the sound emitted by the rotary part 4 that changes depending on the rotational speed, or changes in the rate of flow of the drive fluid. The structure of the device 42 corresponds to the structure of the device 32 described in FIG. 8.

According to another embodiment, the device 42 for determining the rotational speed of the rotary part 4 is implemented by an optical sensor device 45, which for example detects radiation emitted, reflected, or conducted by or through the rotary part 4 (see FIG. 11). The device 42, for example, comprises a radiation source 49, particularly a light-emitting diode, which emits radiation towards the rotary part 4. A reflector 50 is provided on the rotary part, for example a reflecting metal strip, which reflects at least a part of the radiation to a radiation sensor 51, for example an optical semiconductor, particularly a photodiode. By means of the radiation reflected from the reflector 50 and detected by the sensor 51, the sensor 51 is excited to emit a sensor signal that corresponds to the rotational speed. As described with reference to FIG. 9, the component 42A can again be optionally provided that modifies the sensor signal. The sensor signal is forwarded to the control and/or regulation device 41, which determines the rotational speed based on the sensor signal, compares it to a rotational speed set value, and in case of deviation of the determined rotational speed from the set value uses a, particularly electrical, control and/or regulation signal to operate the actuator element 10.

The supply of electrical energy to the actuator element 10, the device 42 for determining the rotational speed of the rotary part 4 and optionally the component 42A which preferably comprises the control and/or regulation device 41 is carried out by an electrical energy source, preferably located outside the handle 1', via the electric lines 48.

According to one embodiment, the control and/or regulation device 41 for the control and/or regulation of the rotational speed of the rotary part 4 is located at least partly outside the handle 1'.

In FIGS. 10 and 11 the actuator element 10 is disposed in or on the fluid line 5 carrying the drive fluid from the fluid source 46 to the rotary part 4. Of course, it is also possible for actuator element 10 to be located on fluid line 6 returning the drive fluid from the rotary part 4 or on a fluid branch line that connects the fluid lines 5, 6 (see FIGS. 5 and 6).

In FIGS. 10 and 11 actuator element 10 is located in the handpiece 2'. Clearly, it is also possible to place the actuator element 10 in the connecting part 3 of the handle 1'.

The invention is not limited to the embodiments represented here but instead comprises all embodiments that employ or include the basic appropriate functional principle of the invention. In addition, all features of all the embodiments described and illustrated here may be combined with one another.

What is claimed is:

1. A medical or dental, fluid-driven handle, comprising
a rotary part that can be set in rotary motion by a drive fluid, to drive a tool that can be connected to the rotary part,
a fluid line carrying the drive fluid to or from the rotary part or a fluid branch line that is connected to a fluid line for carrying the drive fluid to or from the rotary part, and
a control or regulation circuit that is designed to limit, control or regulate the rotational speed of the rotary part, wherein the control or regulation circuit comprises an electrodynamic converter driven by the rotary part for generation of electrical energy and at least one actuator element that is configured to act on the drive fluid flowing in the fluid line or the fluid branch line, wherein the at least one actuator element is electrically connected to the electrodynamic converter in such a way that the at least one actuator element is supplied with electrical energy generated by the electrodynamic converter in order to carry out an actuation process.

2. The medical or dental, fluid-driven handle according to claim 1, wherein the electrodynamic converter comprises at least a coil and a magnetic element and wherein the magnetic element is located on the rotary part so that the magnetic element can be set in rotary motion by the rotary part.

3. The medical or dental, fluid-driven handle according to claim 2, wherein the at least one coil is wound around a soft magnetic coil core.

4. The medical or dental, fluid-driven handle according to claim 1, wherein the actuator element is designed as one of a valve, a control valve, a proportional valve and a throttle.

5. The medical or dental, fluid-driven handle according to claim 1, wherein the fluid branch line connects the fluid line carrying the drive fluid to the rotary part and the fluid line carrying the drive fluid from the rotary part or that the fluid branch line originates from the fluid line carrying the drive fluid to the rotary part and opens into a hollow chamber of a hollow outer shell of the handle.

6. The medical or dental, fluid-driven handle according to claim 1, wherein the fluid line carrying the drive fluid to or from the rotary part comprises an auxiliary line that bypasses the actuator element, so that at least a part of the drive fluid can bypass the actuator element.

7. The medical or dental, fluid-driven handle according to claim 1, wherein the control or regulation circuit comprises a switching and/or control device designed for the selective supply of the at least one actuator element with electric energy generated by the electrodynamic converter depending on the rotational speed of the rotary part.

8. The medical or dental, fluid-driven handle according to claim 7, wherein the control and/or regulation device comprises a device for determining the rotational speed of the rotary part.

9. The medical or dental, fluid-driven handle according to claim 7, wherein the switching and/or control device comprises a microcontroller that is electrically connected to the electrodynamic converter and is designed to compare a value of the electrical energy generated by the electrodynamic converter with a predetermined limit value and to permit the supply of the actuator element with electrical energy generated by the electrodynamic converter if the value of the electrical energy generated by the electrodynamic converter reaches or exceeds the predetermined value.

10. The medical or dental, fluid-driven handle according to claim 7, wherein the switching and/or control device comprises a radiation source and a radiation receiving sensor, wherein the radiation source can be supplied with electrical energy from the electrodynamic converter and the radiation receiving sensor is disposed in such a way that it receives radiation emitted from the radiation source, so that a circuit can be closed between the electrodynamic converter and the actuator element and the actuator element can be supplied with electrical energy generated by the electrodynamic converter when the sensor detects that the radiation source is emitting radiation or emitting radiation that exceeds a predetermined limit value.

11. The medical or dental, fluid-driven handle according to claim 1, wherein the electrodynamic converter comprises multiple coils, wherein at least a first coil is exclusively provided for the supply of the actuator element with electrical energy, and wherein at least a second coil is exclusively provided for the supply of the switching and/or control device with electrical energy and/or for the generation of a switching and/or control signal for the actuator element.

12. The medical or dental, fluid-driven handle according to claim 1, wherein the control or regulation circuit comprises a device for the rectification of the electrical energy generated by the electrodynamic converter, so that the actuator element and/or the control and/or regulation device can be supplied with direct current.

13. The medical or dental, fluid-driven handle according to claim 1, wherein the entire control or regulation circuit is housed in at least one of the handle and a connecting part that can be connected to the handle, and at least one of the actuator element and the switching and/or control device is independent of an electrical energy source located outside the handle and/or the connecting part.

14. The medical or dental, fluid-driven handle according to claim 1, wherein the control or regulation circuit is designed to limit, to control or to regulate the rotational speed of the rotary part and of the tool to a value in a range from about 300,000-150,000 rpm or to a value in the range from about 275,000-200,000 rpm or to about 250,000 rpm.

15. A method for limiting, controlling or regulating the rotational speed of a medical or dental, fluid-driven handle having a rotary part that can be set in rotary motion by a drive fluid to drive a tool connected to the rotary part, a fluid line carrying the drive fluid to or from the rotary part or a fluid branch line that is connected to the fluid line, and a control or regulation circuit that is designed to limit, to control or to regulate the rotational speed of the rotary part, wherein the control or regulation circuit comprises an electrodynamic converter driven by the rotary part and at least one actuator element that is configured to act on the drive fluid flowing in the fluid line or the fluid branch line, wherein the at least one actuator element is electrically connected to the electrodynamic converter, wherein the method comprises:
  driving the rotary part with the drive fluid;
  generating electrical energy with the electrodynamic converter;
  supplying electrical energy from the electrodynamic converter to the at least one actuator element; and
  acting on the drive fluid flowing in the fluid line or the fluid branch line in an actuation process with the actuator element to limit, control or regulate the rotational speed.

* * * * *